United States Patent
Shu et al.

(10) Patent No.: US 10,793,588 B2
(45) Date of Patent: Oct. 6, 2020

(54) CRYSTAL FORM OF SODIUM-GLUCOSE COTRANSPORTER 2 INHIBITOR

(71) Applicant: HAINAN XUANZHU PHARMA CO., LTD., Hainan (CN)

(72) Inventors: Chutian Shu, Shandong (CN); Zhenhua Wang, Shandong (CN)

(73) Assignees: JI LIN HUI SHENG BIO-PHARMACEUTICAL CO., LTD., Jilin (CN); BEIJING HUIZHIHENG BIOTECHNOLOGY CO., LTD., Beijing (CN)

( * ) Notice: Subject to any disclaimer, the term of this patent is extended or adjusted under 35 U.S.C. 154(b) by 63 days.

(21) Appl. No.: 16/305,304

(22) PCT Filed: May 27, 2017

(86) PCT No.: PCT/CN2017/086269
§ 371 (c)(1),
(2) Date: Nov. 28, 2018

(87) PCT Pub. No.: WO2017/206827
PCT Pub. Date: Dec. 7, 2017

(65) Prior Publication Data
US 2020/0131216 A1    Apr. 30, 2020

(30) Foreign Application Priority Data
May 28, 2016    (CN) .......................... 2016 1 0369705

(51) Int. Cl.
*C07H 7/04*    (2006.01)

(52) U.S. Cl.
CPC ............ *C07H 7/04* (2013.01); *C07B 2200/13* (2013.01)

(58) Field of Classification Search
CPC ...................................................... C07H 7/04
See application file for complete search history.

(56) References Cited

U.S. PATENT DOCUMENTS

| | | | |
|---|---|---|---|
| 6,774,112 B2 | 8/2004 | Gougoutas | |
| 7,919,598 B2 * | 4/2011 | Gougoutas | C07H 15/207 536/1.11 |
| 8,507,450 B2 | 8/2013 | Eckhardt et al. | |
| 9,006,403 B2 | 4/2015 | Liou et al. | |
| 9,145,434 B2 | 9/2015 | Eckhardt et al. | |
| 9,562,029 B2 | 2/2017 | Wu | |
| 2015/0191502 A1 * | 7/2015 | Wu | A61K 31/7004 514/23 |

FOREIGN PATENT DOCUMENTS

| CN | 104761522 A | 7/2015 |
|---|---|---|
| EP | 2891654 A1 | 7/2015 |
| JP | 2004536047 A | 12/2004 |
| JP | 2009507809 A | 2/2009 |
| JP | 2012500803 A | 1/2012 |
| JP | 2014520163 A | 8/2014 |
| JP | 2015522644 A | 8/2015 |

OTHER PUBLICATIONS

Definition of prevent, Oxford English Dictionary Online, http://dictionary.oed.com/, accessed online Mar. 27, 2010, especially definition 9a. at p. 2. (Year: 2010).*
Entry for Diabetes, Mayo Clinic web site, dated Juentry for Diabetes, Mayo Clinic web site, dated Jul. 31, 2014, http://www.mayoclinic.org, accessed online on Oct. 17, 2019. (Year: 2014).*
English language abstract for JP 2004-536047 extracted from espacenet.com database on Feb. 6, 2020, 2 pages.
English language abstract for JP 2009-507809 extracted from espacenet.com database on Feb. 6, 2020, 1 page.
English language abstract for JP 2012-500803 extracted from espacenet.com database on Feb. 6, 2020, 2 pages.
English language abstract for JP 2014-520163 extracted from espacenet.com database on Feb. 6, 2020, 1 page.
English language abstract for JP 2015-522644 extracted from espacenet.com database on Feb. 6, 2020, 1 page.
English language abstract and machine-assisted English translation for CN 104761522 extracted from espacenet.com database on Dec. 5, 2018, 33 pages.
International Search Report for Application No. PCT/CN2017/0862694 dated Sep. 4, 2017, 4 pages.

* cited by examiner

*Primary Examiner* — Jonathan S Lau
(74) *Attorney, Agent, or Firm* — Howard & Howard Attorneys PLLC

(57) ABSTRACT

The present invention relates to a crystalline form of a co-crystal of an inhibitor against sodium-glucose cotransporter 2 with L-proline, a method for preparing the same, a pharmaceutical composition comprising the same, and use thereof. Specifically, the present invention relates to a crystalline form of a co-crystal of an inhibitor against sodium-glucose cotransporter 2 represented by formula (1), i.e., (2S,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol, with L-proline, a method for preparing the same, a pharmaceutical composition comprising the same, and use thereof.

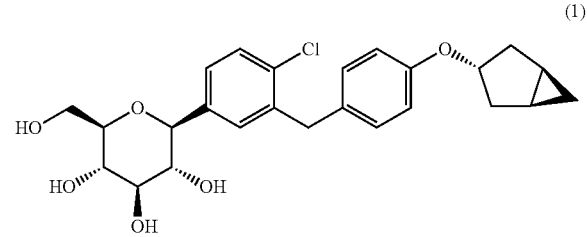

(1)

18 Claims, 2 Drawing Sheets

CRYSTAL FORM OF SODIUM-GLUCOSE COTRANSPORTER 2 INHIBITOR

CROSS-REFERENCE TO RELATED APPLICATIONS

The present application is the National Stage of International Patent Application No. PCT/CN2017/086269, filed on May 27, 2017, which claims priority to and all the benefits of Chinese Application No. 201610369705.X, filed on May 28, 2016, which are hereby expressly incorporated herein by reference in their entirety.

TECHNICAL FIELD

The present invention relates to a crystalline form of a co-crystal of an inhibitor against sodium-glucose cotransporter 2 with L-proline, a method for preparing the same, a pharmaceutical composition thereof, and use thereof in the manufacture of a medicament for treating and/or preventing non-insulin dependent diabetes mellitus and a complication thereof, an insulin resistance disease and/or obesity.

BACKGROUND ART

Sodium-glucose cotransporter 2 (SGLT-2) is a novel therapeutic target for diabetes, and its inhibitor can treat hyperglycemia by inhibiting the reuptake of renal glucose by acting on the SGLT-2, providing a new pathway for treating diabetes. Although this pathway does not directly affect the pathophysiology of type II diabetes, it reduces blood glucose level by enhancing glucose excretion in the kidney, causes a lack of net energy, promotes body weight loss, and indirectly improves obesity symptoms. Compared with other antidiabetic drugs, SGLT-2 inhibitors have the following advantages: improving beta-cell function; improving insulin resistance; reducing the possibility of sodium-water retention; and reducing the risk of causing cardiovascular diseases. The compound of the Formula (1), i.e., (2S,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol (hereafter referred to as the compound of Formula (1) in the description, and, which has been described in the patent application CN 201410004395.2) is a SGLT-2 inhibitor with a very high selectivity for SGLT-2 and good pharmacokinetic properties in vivo.

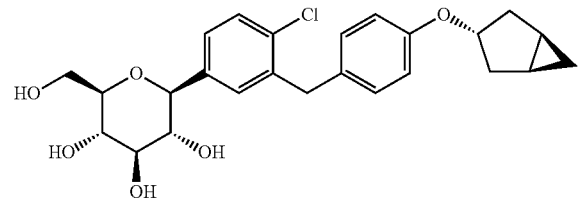
(1)

The research of crystalline forms plays an important role in the development process of drugs. In order to meet the requirements of preparations, production, transportation, etc., the crystalline forms of the compound of Formula (1) have been studied in order to find a crystalline form with good properties.

Contents of the Invention

The inventors of the invention discovered a co-crystal of the compound of Formula (1) with L-proline during the study of the compound of Formula (1), wherein the co-crystal is crystalline Form I.

The present invention relates to a crystalline form of a co-crystal of a SGLT-2 inhibitor represented by Formula (1), i.e., (2S,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol, with L-proline. The present invention also relates to a method for preparing the crystalline form, a pharmaceutical composition comprising the crystalline form, and the use of the crystalline form in the prevention and/or treatment of non-insulin dependent diabetes mellitus and a complication thereof, an insulin resistance disease and/or obesity.

The present invention provides crystalline Form I of a co-crystal of the compound of Formula (1) with L-proline, wherein the molar ratio of the compound of Formula (1) to L-proline is from 1:3 to 1:1, preferably 1:2.

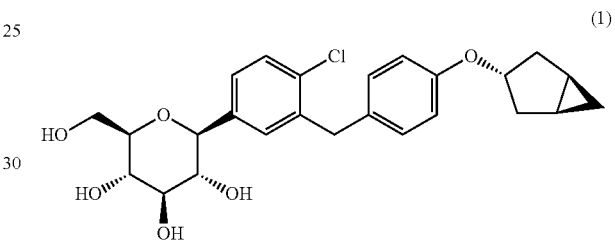
(1)

The present invention provides crystalline Form I of a co-crystal of the compound of Formula (1) with L-proline, wherein the crystalline Form I exhibits an X-ray powder diffraction pattern having characteristic peaks at the 2θ positions of 4.0±0.2°, 17.9±0.2°, 18.5±0.2° and 19.7±0.2°, as determined by using Cu-Kα radiation.

In a preferable embodiment, the X-ray powder diffraction pattern of the crystalline Form I of the co-crystal of the compound of Formula (1) with L-proline further has characteristic peaks at the 2θ positions of 12.5±0.2°, 13.7±0.2° and 15.0±0.2°, in addition to the above characteristic peaks, as determined by using Cu-Kα radiation.

In a preferable embodiment, the X-ray powder diffraction pattern of the crystalline Form I of the co-crystal of the compound of Formula (1) with L-proline further has characteristic peaks at the 2θ positions of 11.3±0.2°, 16.5±0.2° and 24.2±0.2°, in addition to the above characteristic peaks, as determined by using Cu-Kα radiation.

In a preferable embodiment, the X-ray powder diffraction pattern of the crystalline Form I of the co-crystal of the compound of Formula (1) with L-proline further has characteristic peaks at the 2θ positions of 15.5±0.2°, 19.0±0.2° and 22.7±0.2°, in addition to the above characteristic peaks, as determined by using Cu-Kα radiation.

In a preferable embodiment, the X-ray powder diffraction pattern of the crystalline Form I of the co-crystal of the compound of Formula (1) with L-proline is substantially the same as FIG. 1, as determined by using Cu-Kα radiation.

In a preferable embodiment, the crystalline Form I of the co-crystal of the compound of Formula (1) with L-proline exhibits a differential scanning calorimetry thermogram having an endothermic conversion peak at the range from about 130° C. to 170° C., preferably from 140° C. to 160°

C., more preferably exhibits a differential scanning calorimetry thermogram substantially shown in FIG. 2.

In a preferable embodiment, the crystalline Form I of the co-crystal of the compound of Formula (1) with L-proline exhibits a thermogravimetric analysis curve substantially shown in FIG. 3.

The present invention also provides a method for preparing a co-crystal of the compound of Formula (1) with L-proline.

The method for producing the crystalline Form I of the co-crystal of the compound of Formula (1) with L-proline comprises a step of reacting L-proline with the compound of Formula (1). Specifically, the crystalline Form I can be prepared by any of the following two methods.

The method (1) for preparing the crystalline Form I of the co-crystal of the compound of Formula (1) with L-proline may include the following steps:

Dissolving the compound of Formula (1) and L-proline in a single solvent or a mixed solvent under a heating condition to produce a solution, then heating the solution to a certain temperature and maintaining the temperature for a certain period of time; cooling the solution to form a crystal, then isolating and drying the crystal to obtain the crystalline Form I of the co-crystal of the compound of Formula (1) with L-proline.

The term "single solvent" means a solvent that contains only one component, and mainly refers to a good solvent, including but not limited to alcohols, ketones, esters, nitriles, and oxygen-containing heterocycles. For example, the solvent may be selected from alcohols, preferably lower alcohols, more preferably methanol, ethanol, propanol, isopropanol, n-butanol, isobutanol or tert-butanol, further preferably ethanol or isopropanol; or the solvent may be selected from esters, preferably fatty esters, more preferably methyl formate, ethyl formate, propyl formate, isopropyl formate, methyl acetate, ethyl acetate, propyl acetate, isopropyl acetate, methyl propionate, ethyl propionate, propyl propionate, isopropyl propionate, butyl acetate, or isobutyl acetate, further preferably ethyl acetate or isopropyl acetate; or the solvent may be selected from ketones, preferably acetone, butanone, pentanone, methyl butyl ketone or methyl isobutyl ketone, further preferably acetone or butanone; the solvent may be selected from nitriles, preferably acetonitrile; or the solvent may be selected from oxygen-containing heterocycles, preferably tetrahydrofuran, dihydropyran, tetrahydropyran or 1,4-dioxane, more preferably tetrahydrofuran or 1,4-dioxane.

The term "mixed solvent" refers to a mixture consisting of two or more solvents in a certain volume ratio, including but not limited to the following mixed solvent systems: alcohol/water, ketone/water, ether/water, nitrile/water, oxygen-containing heterocyclic/water, alcohol/ester, alcohol/ether, alcohol/alkane, ester/ether or ester/alkane, preferably alcohol/water, ketone/water, nitrile/water or oxygen-containing heterocyclic/water, further preferably lower alcohol/water or ketone/water, more further preferably ethanol/water, acetone/water, isopropanol/water, tetrahydrofuran/water or acetonitrile/water, and the volume ratio may be, for example, from 30:1 to 5:1, preferably from 26:1 to 6:1, preferably from 26:1 to 8:1.

The "certain temperature" in the expression "heating the solution to a certain temperature" in the above method means from 40° C. to 90° C., preferably from 50° C. to 85° C.

The "certain period of time" in the expression "maintaining the temperature for a certain period of time" described in the above method means from 20 to 90 minutes, preferably from 20 to 60 minutes, more preferably from 20 to 40 minutes.

The method (1) for preparing the crystalline Form I of the co-crystal of the compound of Formula (1) with L-proline may include the following steps:

Dissolving the compound of Formula (1) and L-proline in an alcohol, a ketone, a mixed solvent of an alcohol and water or a mixed solvent of a ketone and water under heating to produce a solution, then heating the solution to a temperature of 40° C.-90° C., and maintaining the temperature for 20-90 minutes; cooling the solution to form a crystal, then isolating and drying the crystal to obtain the crystalline Form I of the co-crystal of the compound of Formula (1) with L-proline.

The method (1) for preparing the crystalline Form I of the co-crystal of the compound of Formula (1) with L-proline may include the following steps:

Dissolving the compound of Formula (1) with L-proline in a lower alcohol or a mixed solvent of a lower alcohol and water under a heating condition to produce a solution, then heating the solution to a temperature of 40° C.-90° C., and maintaining the temperature for 20-60 minutes; cooling the solution to form a crystal, then isolating and drying the crystal to obtain the crystalline Form I of the co-crystal of the compound of Formula (1) with L-proline.

The method (1) for preparing the crystalline Form I of the co-crystal of the compound of Formula (1) with L-proline may include the following steps:

Dissolving the compound of the Formula (1) and L-proline in a lower alcohol or a mixed solvent of a lower alcohol and water in a ratio of from 30:1 to 5:1 under a heating condition to produce a solution, then heating the solution to a temperature of 40° C.-90° C., and maintaining the temperature for 20-60 minutes; cooling the solution to form a crystal, then isolating and drying the crystal to obtain the crystalline Form I of the co-crystal of the compound of Formula (1) with L-proline.

The method (1) for preparing the crystalline Form I of the co-crystal of the compound of Formula (1) with L-proline may include the following steps:

Dissolving the compound of the Formula (1) and L-proline in a molar ratio of from 1:4 to 4:1 in a lower alcohol or a mixed solvent of a lower alcohol and water in a ratio of from 26:1 to 6:1 under a heating condition to produce a solution, then heating the solution to a temperature of 50° C.-85° C., and maintaining the temperature for 20-40 minutes; cooling the solution to form a crystal, then isolating and drying the crystal to obtain the crystalline Form I of the co-crystal of the compound of Formula (1) with L-proline.

The method (1) for preparing the crystalline Form I of the co-crystal of the compound of Formula (1) with L-proline may include the following steps: dissolving the compound of the Formula (1) and L-proline in a molar ratio of from 1:3 to 1:1 in a lower alcohol or a mixed solvent of a lower alcohol and water in a ratio of from 26:1 to 8:1 under a heating condition to produce a solution, then heating the solution a temperature of 50° C.-85° C., and maintaining the temperature for 20-40 minutes; cooling the solution to form a crystal, then isolating and drying the crystal to obtain the crystalline Form I of the co-crystal of the compound of Formula (1) with L-proline.

The method (2) for preparing the crystalline Form I of the co-crystal of the compound of Formula (1) with L-proline may include the following steps:

Dissolving the compound of the Formula (1) and L-proline in a single solvent or a mixed solvent under a heating condition, and adding an organic thereto to produce a solution; cooling the solution to form a crystal, then isolating and drying the crystal to obtain the crystalline Form I of the co-crystal of the compound of Formula (1) with L-proline.

The terms "single solvent" and "mixed solvent" in the method (2) are as described in the above in the method (1).

The "organic solvent" described in the methods includes, but is not limited to, alcohols, ketones, esters, ethers, nitriles, alkanes, and any mixed solvents of the above organic solvents. For example, the organic solvent may be selected from alcohols, preferably lower alcohols, more preferably methanol, ethanol, propanol, isopropanol, n-butanol, isobutanol or tert-butanol, further preferably ethanol or isopropanol; or the organic solvent may be selected from esters, preferably fatty esters, more preferably methyl formate, ethyl formate, propyl formate, isopropyl formate, methyl acetate, ethyl acetate, propyl acetate, isopropyl acetate, methyl propionate, ethyl propionate, propyl propionate, isopropyl propionate, butyl acetate or isobutyl acetate, further preferably ethyl acetate or isopropyl acetate; or the organic solvent may be selected from ketones, preferably acetone, butanone, pentanone, methyl butyl ketone or methyl isobutyl ketone, further preferably acetone or butanone; or the organic solvent may be selected from ethers, preferably isopropyl ether, methyl tert-butyl ether, ethyl tert-butyl ether, methyl t-amyl ether, tetrahydrofuran or 1,4-dioxane, further preferably methyl tert-butyl ether, tetrahydrofuran or 1,4-dioxane; or the organic solvent may be selected from nitriles, preferably acetonitrile; or the organic solvent may be selected from alkanes, preferably saturated hydrocarbons, more preferably, n-pentane, isopentane, n-hexane, isohexane or cyclohexane, more preferably n-hexane or cyclohexane; the mixed solvent of the above organic solvents includes, but is not limited to, alcohol/ester, alcohol/ether, alcohol/alkane, ester/ether, ester/alkanes; for example, the mixed solvent may be alcohol/ester, preferably ethanol/ethyl acetate or methanol/ethyl acetate; or the mixed solvent may be alcohol/ether, preferably ethanol/diethyl ether; or the mixed solvent may be alcohol/alkane, preferably alcohol/saturated hydrocarbon, more preferably ethanol/n-hexane; or the mixed solvent may be ester/ether, preferably ethyl acetate/diethyl ether; and the mixed solvent may be ester/alkane, preferably ester/saturated alkane, more preferably ethyl acetate/n-hexane.

The method (2) for preparing the crystalline Form I of the co-crystal of the compound of Formula (1) with L-proline may include the following steps:

Dissolving the compound of the Formula (1) and L-proline in an alcohol, a ketone, a mixed solvent of an alcohol and water or a mixed solvent of a ketone and water under heating, and adding an alkane solvent thereto to produce a solution; cooling the solution to form a crystal, then isolating and drying the crystal to obtain the crystalline Form I of the co-crystal of the compound of Formula (1) with L-proline.

The method (2) for preparing the crystalline Form I of the co-crystal of the compound of Formula (1) with L-proline may include the following steps:

Dissolving the compound of the Formula (1) and L-proline in molar ratio of from 1:4 to 4:1, more preferably from 1:4 to 2:1 in an alcohol or a mixed solvent of an alcohol and water under heating, and adding a saturated hydrocarbon solvent thereto to produce a solution; cooling the solution to form a crystal, then isolating and drying the crystal to obtain the crystalline Form I of the co-crystal of the compound of Formula (1) with L-proline.

The method (2) for preparing the crystalline Form I of the co-crystal of the compound of Formula (1) with L-proline may include the following steps:

Dissolving the compound of the Formula (1) and L-proline in molar ratio of from 1:4 to 4:1, more preferably from 1:4 to 2:1 in an alcohol or a mixed solvent of an alcohol and water in a ratio of from 30:1 to 5:1 under heating, and adding a saturated hydrocarbon solvent thereto to produce a solution; cooling the solution to form a crystal, then isolating and drying the crystal to obtain the crystalline Form I of the co-crystal of the compound of Formula (1) with L-proline.

The method (2) for preparing the crystalline Form I of the co-crystal of the compound of Formula (1) with L-proline may include the following steps:

Dissolving the compound of the Formula (1) and L-proline in molar ratio of from 1:3 to 1:1 in a mixed solvent of an alcohol and water in a ratio of from 26:1 to 6:1 under heating, and adding a saturated hydrocarbon solvent thereto to produce a solution; cooling the solution to form a crystal, then isolating and drying the crystal to obtain the crystalline Form I of the co-crystal of the compound of Formula (1) with L-proline.

The method (2) for preparing the crystalline Form I of the co-crystal of the compound of Formula (1) with L-proline may include the following steps:

Dissolving the compound of the Formula (1) and L-proline in molar ratio of from 1:3 to 1:1 in a mixed solvent of an alcohol and water in a ratio of from 26:1 to 8:1 under heating, and adding a saturated hydrocarbon solvent thereto to produce a solution; cooling the solution to form a crystal, then isolating and drying the crystal to obtain the crystalline Form I of the co-crystal of the compound of Formula (1) with L-proline.

The method (2) for preparing the crystalline Form I of the co-crystal of the compound of Formula (1) with L-proline may include the following steps:

Dissolving the compound of the Formula (1) and L-proline in molar ratio of from 1:3 to 1:1 in a mixed solvent of an ethanol and water in a ratio of from 26:1 to 8:1 under heating, and adding a saturated hydrocarbon solvent thereto to produce a solution; cooling the solution to form a crystal, then isolating and drying the crystal to obtain the crystalline Form I of the co-crystal of the compound of Formula (1) with L-proline.

The drying described in the above methods can be carried out by pressure reduction or ventilation, and the drying can be carried out at a temperature not above 60° C., preferably from 30° C. to 55° C., more preferably from 35° C. to 50° C.

The "cooling" in the expression that "cooling the solution to form a crystal" described in the above methods means that the temperature is lowered to from 10° C. to 30° C.

The "isolating" described in the above methods can be carried out by conventional methods, e.g., filtration etc.

X-ray diffraction is usually employed to analyze the obtained crystals.

When the crystalline form of the present invention is measured by X-ray powder diffraction, sometimes there may be a slight measurement error for the measured peaks due to measurement instrument or measurement conditions, and crystals corresponding to spectra within the error range are also covered in the scope of the crystals of the present invention. Therefore, this error should be taken into consideration when a crystal structure is determined, and the applicant has considered the error range) (±0.2° when determining the degrees 2θ.

The present invention further provides a pharmaceutical composition comprising the crystalline Form I of the co-crystal of the compound of Formula (1) with L-proline and one or more pharmaceutically acceptable carrier and/or diluent, wherein the pharmaceutical composition can be present in any pharmaceutically acceptable dosage form, and can be administered to a patient in need thereof by oral, parenteral, rectal or pulmonary delivery, etc. When orally administered, the pharmaceutical composition can be formulated into a conventional solid preparation such as a tablet, a capsule, a pill, a granule or the like, or an oral liquid preparation such as an oral solution, an oral suspension, a syrup or the like. When an oral preparation is prepared, a suitable filler, a binder, a disintegrant, a lubricant, or the like may be added. When parenterally administered, the pharmaceutical composition can be formulated into an injection, including an injection solution, a sterile powder for injection, and a concentrated solution for injection. When an injection is prepared, the injection can be produced by a conventional method in the pharmaceutical field, and when the injection is formulated, an additional agent may not be added, or a suitable additive may be added depending on the properties of the drug. When rectally administered, the pharmaceutical composition can be formulated into a suppository or the like. When the pharmaceutical composition is administered via pulmonary delivery, it can be formulated into an inhalant or a spray.

The present invention further provides a use of the crystalline Form I of the co-crystal of the compound of Formula (1) with L-proline in the manufacture of a medicament for treating and/or preventing non-insulin dependent diabetes mellitus, hyperglycemia, hyperlipidemia, an insulin resistance disease and/or obesity.

The present invention further provides a method for treating and/or preventing non-insulin dependent diabetes mellitus or a complication thereof, an insulin resistance disease and/or obesity, comprising administering to a patient in need thereof the crystalline Form I of the co-crystal of the compound of Formula (1) with L-proline.

The present invention further encompasses the crystalline Form I of the co-crystal of the compound of Formula (1) with L-proline for use in the treatment and/or prevention of non-insulin dependent diabetes mellitus or a complication thereof, an insulin resistance disease and/or obesity.

The diabetic complication includes, but is not limited to, diabetic nephropathy, a diabetic ocular complication, diabetic foot, a diabetic cardiovascular complication, a diabetic cerebrovascular disease and diabetic neuropathy.

The main advantages of the co-crystal of the compound of Formula (1) with L-proline of the present invention include:

(1) The method for preparing the co-crystal of the compound (2S,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol with L-proline provided by the present invention is easily operated and suitable for industrial production;

(2) The co-crystal of L-proline provided by the present invention has good properties and flowability, and is convenient for testing, preparation, transportation and storage;

(3) The co-crystal of L-proline provided by the present invention has a high purity, less residual solvent, high solubility, good dissolution, good stability and easily controlled quality;

(4) The co-crystal of L-proline provided by the present invention has an excellent bioavailability;

(5) The co-crystal of L-proline provided by the present invention has a good hypoglycemic effect and can be used for treating and/or preventing non-insulin dependent diabetes mellitus.

SPECIFIC MODE FOR CARRYING OUT THE INVENTION

Figure 1:
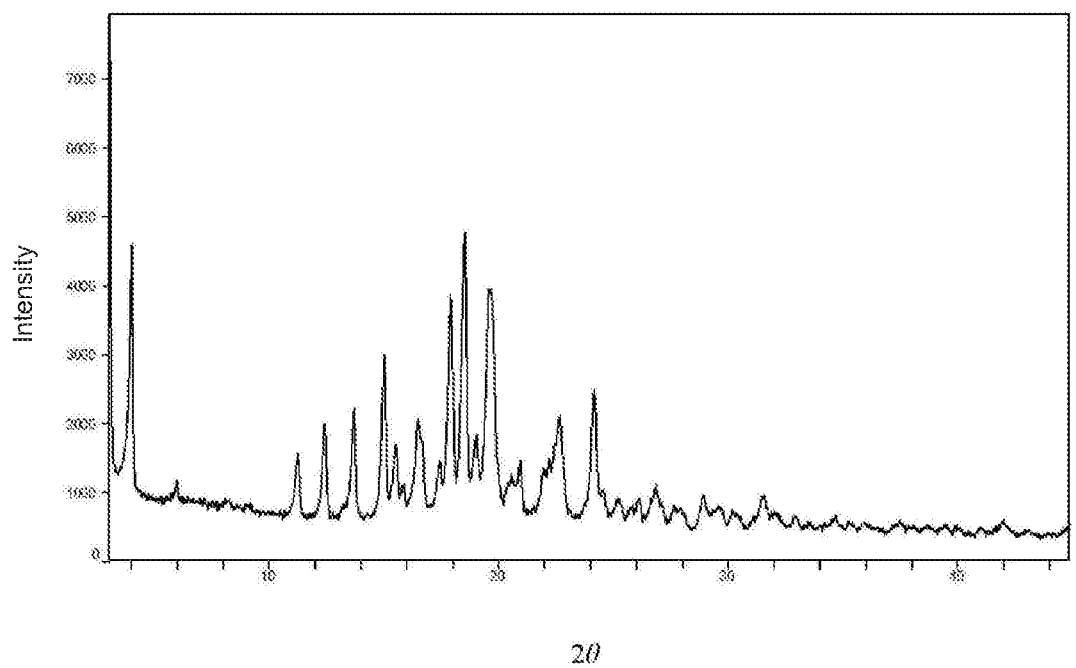
FIG. 1 is an X-ray powder diffraction pattern of the crystalline Form I of the co-crystal of the compound of Formula (1) with L-proline, wherein the ordinate indicates the diffraction intensity and the abscissa indicates the diffraction angle (2θ).

The above contents of the present invention will be further described in detail below by way of specific embodiments in the form of examples. However, it should not be understood that the scopes of the above-described subject matters of the present invention are limited to the following examples. All techniques implemented in accordance with the above-described contents of the present invention are within the scope of the present invention.

Example 1 Preparation of the Crystalline Form I of the Co-Crystal of the Compound of Formula (1) with L-proline (1)

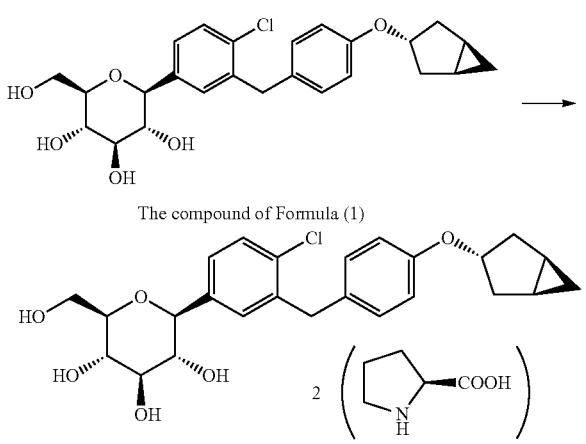

The co-crystal of the compound of Formula (1) and L-proline

The compound of Formula (1) (1478 g, 3.21 mol) and L-proline (739 g, 6.42 mol) were placed in a 10 L round bottom flask, then 7094 mL of ethanol and 784 mL of water were added thereto under mechanically stirring, and the raw materials were heated and quickly dissolved. When the temperature was raised to 30° C., a white solid precipitated. The temperature was further raised to 80° C., and the solvent began to reflux and the solution became clear. After refluxed for half an hour, the solution was slowly cooled to 29° C. to precipitate a solid, and continued to cool down and stood overnight. After suction filtration, the filter cake was washed with a mixed solvent of cold ethanol:water=9:1 (750 mL×2), and dried under vacuum at 40° C. to give 1806 g of solid, with a yield of 81.5%. The resulting solid was determined by XRPD as crystalline Form I.

Example 2 Preparation of the Crystalline Form I of the Co-Crystal of the Compound of Formula (1) with L-proline (2)

The compound of Formula (1) (200 mg, 0.43 mmol) was placed in a 100 mL round bottom flask, then 1.5 mL of isopropyl alcohol was added thereto, and the mixture was heated to 58° C. to be dissolved. To L-proline (50 mg, 0.43 mmol) in a container, 2 mL of a mixed solvent of isopropanol:water=24:1 was added to dissolve L-proline, and the L-proline solution was added dropwise to the round bottom flask. The container was washed with 0.5 mL of a mixed solvent of isopropanol:water=24:1 and the washing solution was poured in the round bottom flask. After 2 minutes, a white solid precipitated. The temperature was maintained at 55° C. for 30 minutes, and then lowered to 14° C. After filtration, the filter cake was dried under vacuum at 35° C. to give 125 mg of solid, with a yield of 50%. The resulting solid was determined by XRPD as crystalline Form I.

Example 3 Preparation of the Crystalline Form I of the Co-Crystal of the Compound of Formula (1) with L-proline (3)

To the compound of Formula (1) (230 mg, 0.5 mmol) and L-proline (115 mg, 1.0 mmol), 1.46 mL of ethanol and 0.16 mL of water were added, and a white solid precipitated immediately after dissolution. The temperature was raised and the solution gradually became clear and began to reflux. To the solution, 0.20 mL of n-hexane was added dropwise, and there was no significant change. After 7 minutes of reflux, the solution was cooled, and a solid was formed at 44° C. After the solution was cooled to room temperature, the solution was filtered. The filter cake was dried under vacuum at 35° C. to give 181 mg of solid, with a yield of 52.5%. The resulting solid was determined by XRPD as crystalline Form I.

The Crystalline Form I Prepared by the above Methods was Measured.

Measurement with X-Ray Powder Diffraction

The crystal structure of the present invention is not limited to a crystal structure having an X-ray powder diffraction pattern that is identical to the X-ray powder diffraction pattern shown in the drawings as disclosed in the present application, and any crystal structure having an X-ray powder diffraction pattern that is substantially the same as that disclosed in the drawings is encompassed in the scope of the present invention.

Conditions under which X-ray powder diffraction measurement was carried out: Cu palladium, Kα1 (Å): 1.540598, step size 0.0262, 1 second per step.

The crystalline Form I exhibits an X-ray powder diffraction pattern has characteristic peaks at the 2θ positions of 4.0±0.2°, 17.9±0.2°, 18.5±0.2°, 19.7±0.2°, further has characteristic peaks at 12.5±0.2°, 13.7±0.2°, 15.0±0.2°, further has characteristic peaks at 11.3±0.2°, 16.5±0.2°, 24.2±0.2° and further has characteristic peaks at 15.5±0.2°, 19.0±0.2°, 22.7±0.2°.

The co-crystal of the compound of Formula (1) with L-proline (crystalline Form) had an X-ray powder diffraction pattern substantially shown in FIG. 1, and the crystalline Form I has characteristic peaks at the 2θ positions of: 4.0±0.2°, 11.3±0.2°, 12.5±0.2°, 13.7±0.2°, 15.0±0.2°, 16.5±0.2°, 17.9±0.2°, 18.5±0.2°, 19.7±0.2°, 24.2±0.2°, 15.5±0.2°, 19.0±0.2°, 22.7±0.2°.

Differential Scanning Calorimetry

Figure 2:
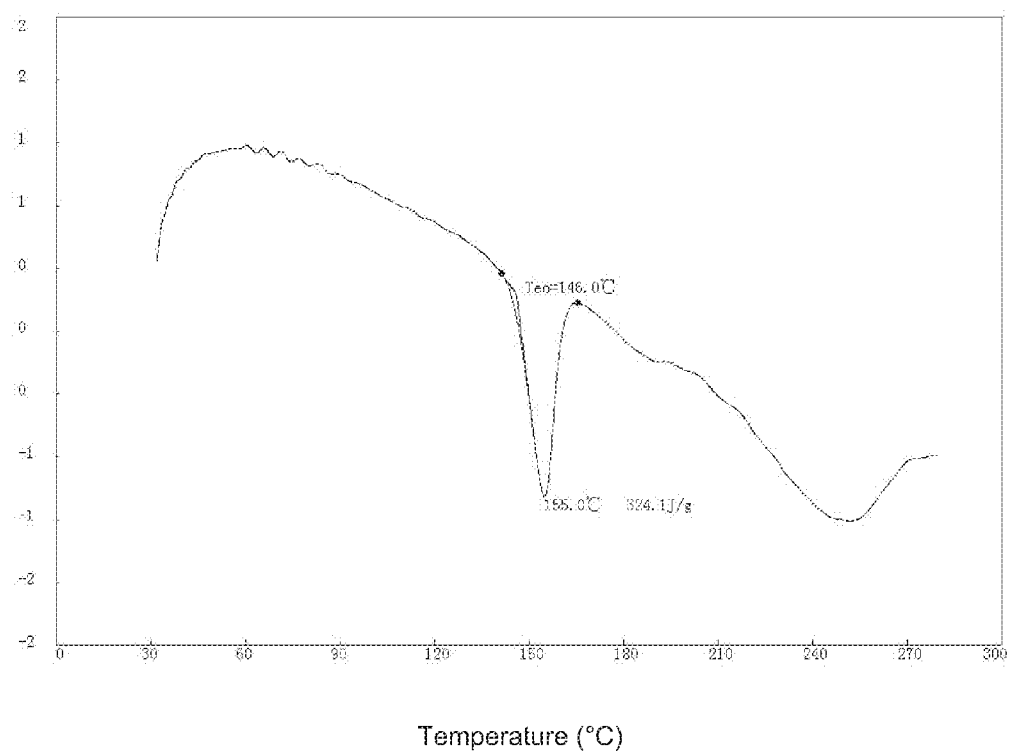
FIG. 2 is a differential scanning calorimetry (DSC) thermogram of the crystalline Form I of the co-crystal of the compound of Formula (1) with L-proline.

The solid state thermal properties of the crystalline Form I of the co-crystal of the compound of Formula (1) with L-proline were studied by differential scanning calorimetry (DSC). The DSC thermogram of the crystalline Form I was shown in FIG. 2.

Measurement conditions: nitrogen was purged at 100 mL/min, heating rate is 10° C./min, data was collected from room temperature to 300° C., and the thermogram was plotted with downward endothermic peaks.

In the DSC measurement, the actually measured start temperature and maximum temperature varied to certain extend depending on the measurement parameters and the heating rate.

Thermogravimetric Analysis

Measurement conditions: nitrogen was purged at 100 mL/min, heating rate is 10° C./min, data was collected from room temperature to 300° C.

Figure 3:
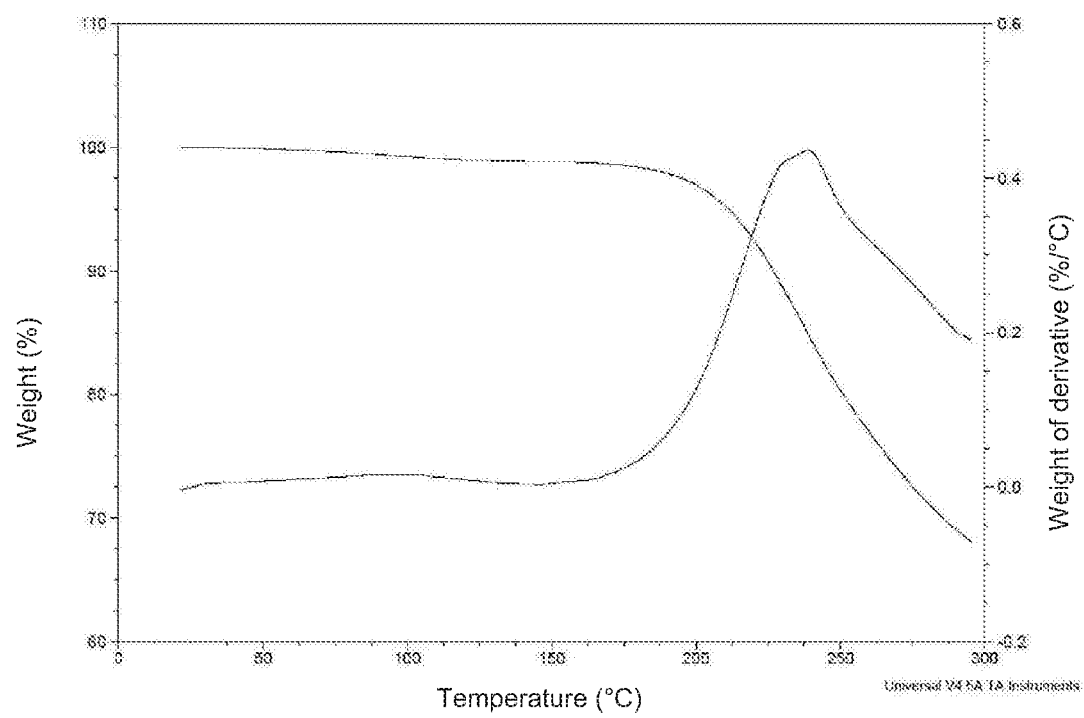
FIG. 3 is a thermogravimetric analysis (TGA) curve of the crystalline Form I of the co-crystal of the compound of Formula (1) with L-proline.

The TGA curve of the crystalline Form I of the co-crystal of the compound of Formula (1) with L-proline was shown in FIG. 3.

Example 4 Test on Stability of the Crystalline Form I of the Co-Crystal of the Compound of Formula (1) with L-proline Test Samples:

The crystalline Form I of the co-crystal of the compound of Formula (1) with L-proline, which was prepared according to the methods in the examples; free compound of Formula (1).

Test Conditions:

The test samples were placed under conditions of 60° C., 40° C., RH 90%±5%, RH 75%±5%, 4500lx±500lx or UV-Vis for 10 days, then sampled on the 5$^{th}$ and 10$^{th}$ days respectively, and the samples were tested for relevant substances and XRD pattern; and the results were compared with those of a sample on the 0$^{th}$ day.

Determination of the relevant substances: the determination was carried out in accordance with High Performance Liquid Chromatography in Appendix V D in Pharmacopoeia of the People's Republic of China (2010) (Volume II).

XRD measurement: the measurement was carried out in accordance with X-Ray Powder Diffraction in Appendix IX F in Pharmacopoeia of the People's Republic of China (2010) (Volume II).

Test Results:

TABLE 1

Results of the stability test of the crystalline Form I

| Test condition | Placement time | Properties | Relevant substances (%) | XRD |
|---|---|---|---|---|
| 60° C. | $0^{th}$ day | Almost white loose mass or powder | 0.60 | — |
|  | $5^{th}$ day | Almost white loose mass or powder | 0.68 | Identical to the XRD pattern in $0^{th}$ day |
|  | $10^{th}$ day | Almost white loose mass or powder | 0.62 | Identical to the XRD pattern in $0^{th}$ day |
| 40° C. | $5^{th}$ day | Almost white loose mass or powder | 0.67 | Identical to the XRD pattern in $0^{th}$ day |
|  | $10^{th}$ day | Almost white loose mass or powder | 0.65 | Identical to the XRD pattern in $0^{th}$ day |
| RH90% ± 5% | $5^{th}$ day | Almost white loose mass or powder | 0.65 | Identical to the XRD pattern in $0^{th}$ day |
|  | $10^{th}$ day | Almost white loose mass or powder | 0.63 | Identical to the XRD pattern in $0^{th}$ day |
| RH75% ± 5% | $5^{th}$ day | Almost white loose mass or powder | 0.66 | Identical to the XRD pattern in $0^{th}$ day |
|  | $10^{th}$ day | Almost white loose mass or powder | 0.64 | Identical to the XRD pattern in $0^{th}$ day |
| 4500 lx ± 500 lx* | $5^{th}$ day | Almost white loose mass or powder | 0.66 | Identical to the XRD pattern in $0^{th}$ day |
|  | $10^{th}$ day | Almost white loose mass or powder | 0.71 | Identical to the XRD pattern in $0^{th}$ day |

TABLE 2

Results of stability test of free compound of Formula (1)

| Test condition | Placement time | Properties | Relevant substances (%) | XRD |
|---|---|---|---|---|
| 60° C. | $0^{th}$ day | Almost white powder | 1.35 | Amorphism |
|  | $10^{th}$ day | Almost white powder | 1.43 | Amorphism |
| 40° C. | $10^{th}$ day | Almost white powder | 1.44 | Amorphism |
| RH90% ± 5% | $6^{th}$ day | Hygroscopic deliquescence | — | Amorphism |
| RH75% ± 5% | $6^{th}$ day | Hygroscopic deliquescence | — | Amorphism |
| UV-Vis* | A period of time that meets the illumination requirement | Tawny powder | 9.91 | Amorphism |

*total illumination of $\geq 1.2 \times 10^6$ Lux · h, near ultraviolet energy of $\geq 200$ w · h/m$^2$ Test Conclusions:

After being placed in the conditions of the above temperature, humidity or light for 10 days, the property, the relevant substances and the XRD pattern of the crystalline Form I of the co-crystal of the compound of Formula (1) with L-proline did not change significantly.

After being placed under the conditions of the above temperature for 10 days, the amount of relevant substances of the free base of the compound of Formula (1) was increased; after being placed under the conditions of the above humidity, the free base sample had a significant hygroscopic deliquescence on the $6^{th}$ day; after being placed under the conditions that meet the illumination requirement, the relevant substances was increased by 8.56% relative to that on the $0^{th}$ day, and the property of the sample changed from an almost white powder to a tawny powder.

It can be seen from the above results that the crystalline Form I of the co-crystal of the compound of the Formula (1) with L-proline had better stability than the free base of the compound, which would help the preparation, transportation and storage of the drug, and ensure the effectiveness and safety of the drug when applied.

Example 5 Test on Residual Solvents of the Crystalline Form I of the Co-Crystal of the Compound of Formula (1) with L-Proline 1. Test Samples The compound of the Formula (1) was obtained according to the preparation method described in pages 10-14 of the description in the CN104761522A (while without treatment with preparative chromatography in the $12^{th}$ step), and the residual amount of ethyl acetate in the compound was determined by gas chromatography. Meantime, the residual amount of ethyl acetate was determined in a co-crystal formed by adding L-proline to the compound of the Formula (1).

2. Test method: the determination was carried out in accordance with the method for determining residual solvents in Appendix VIII P of Pharmacopoeia of the People's Republic of China (2010) (Volume II).

3. Test Results

TABLE 3

Determination results of residual solvent

| Determined item | The compound of Formula (1) | Co-crystal of the compound of Formula (1) with L-proline (crystalline Form I) |
|---|---|---|
| Residual solvent | 0.58% of ethyl acetate | Ethyl acetate was not detected |

The ethyl acetate in the sample of the compound of Formula (1) was not removed after spin-drying treatment, and the amount of the ethyl acetate was over the limit provided in Pharmacopoeia of the People's Republic of China (Volume II). After the compound of Formula (1) formed a co-crystal with L-proline, the residual solvent was effectively removed, and a crystalline form with good properties was obtained, simplifying the post-treatment process, which was conducive to cost saving and quality control, and was conducive to industrialization in the industrial production.

What is claimed is:

1. Crystalline Form I of a co-crystal of the compound of Formula (1) with L-proline, wherein the compound of Formula (1) is (2S,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol, the compound of Formula (1) with L-proline are present in a molar ratio of 1:2, the crystalline Form I exhibits an X-ray powder diffraction pattern having characteristic peaks at the 2θ positions of 4.0±0.2°, 17.9±0.2°, 18.5±0.2° and 19.7±0.2°, as determined by using Cu-Kα radiation,

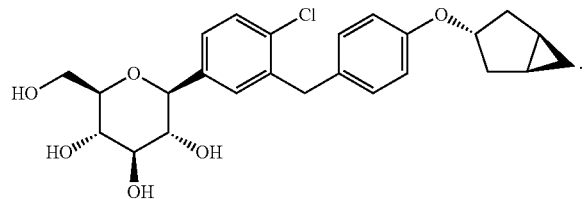

(1)

2. The crystalline Form I according to claim 1, wherein the X-ray powder diffraction pattern further has characteristic peaks at the 2θ positions of 12.5±0.2°, 13.7±0.2° and 15.0±0.2°, as determined by using Cu-Kα radiation.

3. The crystalline Form I according to claim 2, wherein the X-ray powder diffraction pattern further has characteristic peaks at the 2θ positions of 11.3±0.2°, 16.5±0.2° and 24.2±0.2°, as determined by using Cu-Kα radiation.

4. The crystalline Form I according to claim 3, wherein the X-ray powder diffraction pattern further has characteristic peaks at the 2θ positions of 15.5±0.2°, 19.0±0.2° and 22.7±0.2°, as determined by using Cu-Kα radiation.

5. The crystalline Form I according to claim 1, which exhibits a differential scanning calorimetry thermogram having an endothermic conversion peak at the range from 130° C. to 170° C.

6. The crystalline Form I according to claim 5, wherein the differential scanning calorimetry thermogram has the endothermic conversion peak at the range from 140° C. to 160° C.

7. A method for preparing the crystalline Form I according to claim 1, including the steps of: dissolving the compound of the Formula (1) and L-proline in a single solvent or a mixed solvent under a heating condition to produce a solution; then heating the solution to a certain temperature; maintaining the temperature for a certain period of time; cooling the solution to form a crystal; and isolating and drying the crystal to obtain the crystalline Form I.

8. A method for preparing the crystalline Form I according to claim 1, including the steps of: dissolving the compound of the Formula (1) and L-proline in a single solvent or a mixed solvent under a heating condition; adding an organic solvent thereto to produce a solution; cooling the solution to form a crystal; and then isolating and drying the crystal to obtain the crystalline Form I.

9. The method according to claim 7, wherein the single solvent is selected from the group consisting of: alcohols, esters, ketones, nitriles, and oxygen-containing heterocycles, and the mixed solvent is selected from the group consisting of: a mixture of alcohol and water, a mixture of ketone and water, a mixture of nitrile and water, and a mixture of oxygen-containing heterocycle and water.

10. The method according to claim 8, wherein the organic solvent is selected from the group consisting of alcohols, ketones, esters, ethers, nitriles, alkanes, and any mixtures thereof.

11. The method according to claim 9, wherein the single solvent is selected from the group consisting of lower alcohols and ketones.

12. A pharmaceutical composition comprising the crystalline Form I according to claim 1 and one or more pharmaceutically acceptable carrier, wherein the pharmaceutical composition is suitable for being formulated into any of pharmaceutically acceptable dosage forms.

13. The method according to claim 8, wherein the single solvent is selected from the group consisting of: alcohols, esters, ketones, nitriles, and oxygen-containing heterocycles, and the mixed solvent is selected from the group consisting of: a mixture of alcohol and water, a mixture of ketone and water, a mixture of nitrile and water, and a mixture of oxygen-containing heterocycle and water.

14. The method according to claim 9, wherein the single solvent is selected from the group consisting of methanol, ethanol, propanol, isopropanol, n-butanol, isobutanol, tert-butanol, acetone, and butanone.

15. The method according to claim 10, wherein the single solvent is selected from the group consisting of lower alcohols and ketones; and the organic solvent is selected from the group consisting of saturated hydrocarbons and alcohol/saturated hydrocarbon.

16. The method according to claim 15, wherein the single solvent is selected from the group consisting of methanol, ethanol, propanol, isopropanol, n-butanol, isobutanol, tert-butanol, acetone, and butanone.

17. The method according to claim 15, wherein the organic solvent is selected from the group consisting of n-pentane, isopentane, n-hexane, isohexane, cyclohexane, and ethanol/n-hexane.

18. A method for treating non-insulin dependent diabetes mellitus or a complication thereof, an insulin resistance disease or obesity, comprising administering to a patient the crystalline Form I according to claim 1.

* * * * *